United States Patent
Kim et al.

(10) Patent No.: US 10,022,247 B2
(45) Date of Patent: Jul. 17, 2018

(54) AUTOMATIC MACHINE FOR PROCESSING TOOTH INTO BONE GRAFT MATERIAL

(71) Applicant: KOREA DENTAL SOLUTION CO., LTD., Sasang-gu, Busan (KR)

(72) Inventors: Sanghun Kim, Busan (KR); Gyoocheon Kim, Yangsan-si (KR)

(73) Assignee: KOREA DENTAL SOLUTION CO., LTD., Busan (KR)

( * ) Notice: Subject to any disclaimer, the term of this patent is extended or adjusted under 35 U.S.C. 154(b) by 0 days.

(21) Appl. No.: 14/895,158

(22) PCT Filed: Jun. 9, 2014

(86) PCT No.: PCT/KR2014/005053
§ 371 (c)(1),
(2) Date: Dec. 1, 2015

(87) PCT Pub. No.: WO2014/196844
PCT Pub. Date: Dec. 11, 2014

(65) Prior Publication Data
US 2016/0100959 A1    Apr. 14, 2016

(30) Foreign Application Priority Data
Jun. 7, 2013 (KR) .......... 10-2013-0065115

(51) Int. Cl.
*A61F 2/46* (2006.01)
*B08B 3/04* (2006.01)
(Continued)

(52) U.S. Cl.
CPC .......... *A61F 2/4644* (2013.01); *A61C 8/0012* (2013.01); *A61C 19/00* (2013.01);
(Continued)

(58) Field of Classification Search
CPC .......... A61F 2/4644; A61F 2002/4646; A61L 2/0011; A61L 2/0088; A61L 2/025;
(Continued)

(56) References Cited

U.S. PATENT DOCUMENTS 3,352,311 A * 11/1967 Murphy .................... B08B 3/12
134/118
3,392,964 A * 7/1968 Krolik ....................... B08B 3/12
134/121
(Continued)

FOREIGN PATENT DOCUMENTS

| KR | 10-1163594 B1 | 7/2012 |
| KR | 10-1190710 B1 | 10/2012 |
| KR | 10-2012-0144121 | 12/2012 |

OTHER PUBLICATIONS

Machine Translation of KR 10-1190710, Oct. 2012. (Year: 2012).*

*Primary Examiner* — David G Cormier
(74) *Attorney, Agent, or Firm* — Muncy, Geissler, Olds & Lowe, P.C.

(57) ABSTRACT

An automatic machine for processing a tooth by a graft material includes: a body including a power supply supplying power to a controller, which controls the amount of supply solution and operation of a suction pump and a vibrator, and having a receiving space; a receiving container disposed in the receiving space, having a space for keeping a tooth bone graft material, and including a net and a cover having a handle; a cylinder having a space for keeping the receiving container, and inlets and outlets for supplying and discharging the supply solution; a vibrator fastened to the cylinder and generating vibration of 1 to 100,000 VPM; a supplying container supplying the supply solution to the cylinder; and a suction pump discharging solution in the cylinder to a discharging container.

4 Claims, 3 Drawing Sheets

(51) Int. Cl.
  *A61C 19/00*   (2006.01)
  *A61C 8/00*    (2006.01)
  *A61L 2/00*    (2006.01)

(52) U.S. Cl.
  CPC ............ *A61L 2/0011* (2013.01); *A61L 2/0088* (2013.01); *B08B 3/04* (2013.01); *A61F 2002/465* (2013.01); *A61F 2002/4646* (2013.01); *A61F 2240/002* (2013.01)

(58) Field of Classification Search
  CPC ......... A61C 19/00; A61C 19/002; B08B 3/04; B08B 3/044; B08B 3/045; B08B 3/10; B08B 3/102; B08B 3/12
  See application file for complete search history.

(56) References Cited

U.S. PATENT DOCUMENTS

| | | | | |
|---|---|---|---|---|
| 4,409,999 | A | * | 10/1983 | Pedziwiatr ................ B08B 3/12 134/184 |
| 5,113,881 | A | * | 5/1992 | Lin ........................ A23L 3/015 134/1 |
| 5,429,810 | A | | 7/1995 | Knaepler et al. |
| 5,976,104 | A | | 11/1999 | Wolfinbarger, Jr. |
| 6,102,056 | A | * | 8/2000 | Kotsopey ................. B08B 3/10 134/105 |
| 6,719,850 | B2 | * | 4/2004 | Glucksman ............. A47L 25/00 134/1 |
| 2007/0056610 | A1 | * | 3/2007 | Lee ........................ A47J 43/24 134/25.3 |
| 2011/0083708 | A1 | * | 4/2011 | Puskas ..................... B08B 3/12 134/58 R |

\* cited by examiner

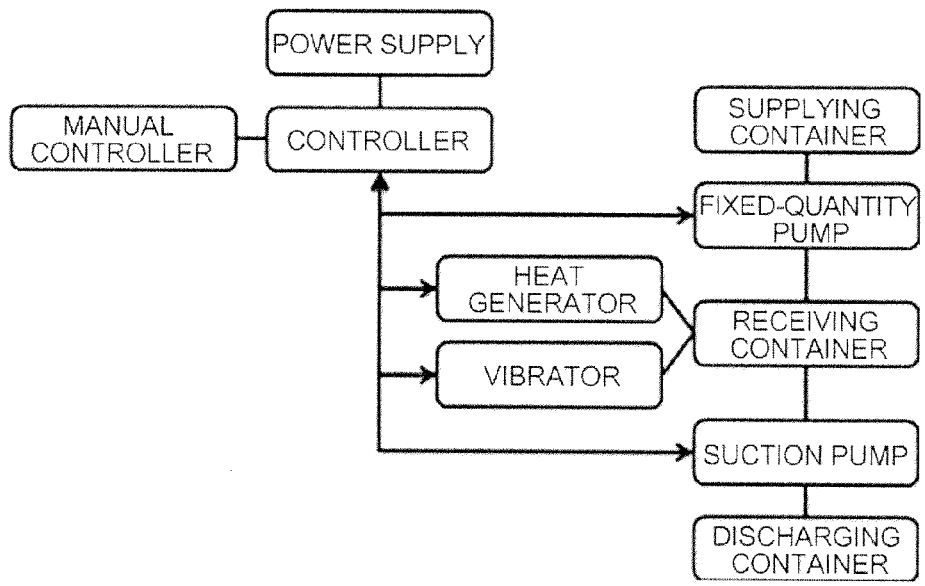

FIG. 5

| BLOCK TYPE | POWDER TYPE | |
|---|---|---|
| PRIMARY STERILIZATION | PRIMARY STERILIZATION | |
| REMOVAL OF FOREIGN SUBSTANCE | REMOVAL OF FOREIGN SUBSTANCE | |
| DESIGN (FORMING)/BORING | | |
| DRYING | DRYING | |
| COATING | CRUSHING | AUTOMATIC MANUFACTURING PROCESS OF THE INVENTION |
| REMOVAL OF INORGANIC SUBSTANCE | REMOVAL OF INORGANIC SUBSTANCE/ REMOVAL OF ORGANIC SUBSTANCE | CHARACTERISTICS OF THE INVENTION |
| REMOVAL OF CHEMICAL/VACUUM SUCTION | REMOVAL OF CHEMICAL/VACUUM SUCTION | 1. REDUCTION OF MANUFACTURING TIME<br>- RELATED ART: 2 HOURS OR MORE<br>- THE INVENTION: 15 MINUTES ~ 1 HOUR |
| NEUTRALIZATION | NEUTRALIZATION | |
| REMOVAL OF CHEMICAL/VACUUM SUCTION | REMOVAL OF CHEMICAL/VACUUM SUCTION | |
| PRIMARY WASHING | PRIMARY WASHING | 2. BACTERIAL CONTAMINATION IS PREVENTED BY AUTOMATED PROCESS |
| REMOVAL OF CHEMICAL/VACUUM SUCTION | REMOVAL OF CHEMICAL/VACUUM SUCTION | |
| REMOVAL OF FAT, REMOVAL OF PROTEIN | REMOVAL OF FAT, REMOVAL OF PROTEIN | 3. BLOCK/POWDER IS AVAILABLE |
| REMOVAL OF CHEMICAL/VACUUM SUCTION | REMOVAL OF CHEMICAL/VACUUM SUCTION | 4. REDUCTION OF MANUFACTURING TIME BY MAGNETIC VIBRATOR<br>- PROCESSED BONE GRAFT MATERIAL CAN BE DIRECTLY USED<br>- PRODUCT CAN BE MANUFACTURED IN SHAPE THAT OPERATOR WANTS |
| SECONDARY WASHING | SECONDARY WASHING | |
| REMOVAL OF CHEMICAL/VACUUM SUCTION | REMOVAL OF CHEMICAL/VACUUM SUCTION | |
| STERILIZATION AND BLEACHING | STERILIZATION AND BLEACHING | |
| REMOVAL OF CHEMICAL/VACUUM SUCTION | REMOVAL OF CHEMICAL/VACUUM SUCTION | |
| THIRD ~ TENTH WASHING | THIRD ~ TENTH WASHING | 5. CONTENTS OF ORGANIC SUBSTANCE/ INORGANIC SUBSTANCE CAN BE ADJUSTED |
| REMOVAL OF CHEMICAL/VACUUM SUCTION | REMOVAL OF CHEMICAL/VACUUM SUCTION | |
| OPERATION OR DRYING | OPERATION OR DRYING | |
| FREEZING-DRYING/STERILIZATION | FREEZING-DRYING/STERILIZATION | |

FIG. 6

AUTOMATIC MACHINE FOR PROCESSING TOOTH INTO BONE GRAFT MATERIAL

BACKGROUND OF THE INVENTION

Field of the Invention

The present invention relates to an automatic machine for processing a tooth into a bone graft material and, more particularly, an automatic machine for processing a tooth into a graft material that can supply a reagent and sterilized distilled water, which can control the contents of organic substances and inorganic substances, in a predetermined amount, with a powder type or a block type graft material in a container, and that includes a heat generator and vibrator for rapidly manufacturing a graft material.

Description of Related Art

The present invention relates to a machine that automatically manufactures a tooth into bone graft material that is used for dental implantation and guided bone regeneration (GBR).

Usability of a bone graft material made from a tooth (hereinafter a tooth bone graft material) has been reported as being successful in many theses and clinical tests, but there is a problem that it is required to entrust enterprises having special facilities in order to make a tooth bone graft material, it takes long time to manufacture a tooth bone graft material due to manual work in the related art, and the cost for transportation is high, so it is difficult to operate on a patient in a short time.

Further, there are two purposes of using a tooth bone graft material. The first purpose is to restore the original shape of a collapsed alveolus by restoring the alveolus after extraction of a tooth. This is for preventing a loss of volume of a graft material while a new bone grows by increasing osteoconduction using a bone graft material containing a large amount of inorganic substances, thereby restoring a collapsed alveolus. The second purpose is to improve osteoinduction that reduces bone restoration time by inducing bone growth factors, by implanting a tooth bone graft material containing a large amount of organic substances into the part with the alveolus removed, which is not related with a loss of volume of a tooth bone graft material, to be absorbed into the existing alveolus in a short time.

In the related art, tooth bone graft materials are manufactured through a predetermined series of simple processes, regardless of the contents of inorganic substances and organic substances in the tooth bone graft materials. When these graft materials are used, medical institutions that treat injured alveoli cannot estimate a reduction ratio of volume of the graft materials and osteoinduction, so they inject an excessive amount of graft material. Accordingly, patients who have had the operation have to stand a pain for a long period of time and the next step of the operation cannot be performed due to slow osteoinduction.

Therefore, there is a need for an automatic machine for manufacturing a tooth bone graft material that can control the contents of inorganic substances and organic substances in a tooth bone graft material in consideration of osteoinduction and osteoconduction, and that reduces the manufacturing time through an automated manufacturing process.

As a countermeasure against the problems, a "method for producing tooth bone graft materials" that uses ultrasonic waves under vacuum has been disclosed in Korean Patent No. 10-1163594. This patent has a problem in that it is difficult to keep a vacuum state while sequentially putting tooth bone graft materials into a chemical, it takes a predetermined time to make a vacuum state again, and graft materials are necessarily formed in a block shape, as in the related art.

Further, block-shaped graft materials containing a large amount of organic substances are low in strength, so they cannot keep the volume after being implanted and are absorbed too quickly, so the treatment purpose cannot be achieved. Furthermore, 80~90% of graft materials for a lost bone are generally used in a powder type, so there is a need for an automatic machine for powder type graft materials.

In addition, since tooth bone graft materials are supposed to be implanted into a human body, there is a need for measures against bacterial contamination in the manufacturing process.

Therefore, there is a need for an automatic machine processing a tooth into a bone graft material that can use a powder type graft material, can control the contents of organic substances and inorganic substances in a graft material, and can prevent bacterial contamination due to manual work in the manufacturing process.

SUMMARY OF THE INVENTION

Technical Problem

The present invention has been made in effort to solve the problems and an object of the present invention is to provide an automatic machine for making a bone graft material from a tooth (tooth bone graft material) that can manufacture a tooth bone graft material not only in a block type, but in a powder type, that can precisely supply a reagent, which can control the contents of organic substances and inorganic substance in the graft material, and that can prevent bacterial contamination in a manufacturing process through automated manufacturing process.

Another object of the present invention is to provide an automatic machine for a tooth graft material that can reduce a manufacturing time at a level of ⅓ ~ 1/10 of the related art to directly operate a patient.

Technical Solution

In order to achieve the objects, the present invention provides an automatic machine for processing a tooth into a bone graft material, the automatic machine including: a body 10 including a power supply 60 supplying power to a controller that controls the amount of a supply solution, and operation of a suction pump 40 and a vibrator 80, the bodying 10 having a receiving space defined by a frame; a receiving container 53 disposed in the receiving space, having a space for keeping a tooth bone graft material, and including a net 59, through which the supply solution can flow inside, and a cover 51 having a handle 52 for convenience work; a cylinder 55 having a space for keeping the receiving container 53, inlets 56 for supplying the supply solution, and outlets 57 for discharging the supply solution; a vibrator 80 fastened to a side of the cylinder 55 and generating vibration of 1 to 100,000 VPM; a supplying container 20 for supplying the supply solution to the cylinder 55; and a suction pump 40 discharging a solution in the cylinder 55 to a discharging container 70.

Further, in the automatic machine, the vibrator 80 may include a vibrator directly fastened to the cylinder 55 using an electromagnet, and a spring 81.

Further, in the automatic machine for processing a tooth into a bone graft material, a net 59 of the receiving container 53 may have fine holes of 1 to 2,000 micron.

The automatic machine for processing a tooth into a bone graft material may further include a heat generator 54 covering the cylinder 55 and the supplying container 20 to heat the supply solution therein.

The machine may further include a fixed-quantity pump 30 supplying the supply solution in the supplying container 20 in a predetermined amount, between the supplying container 20 and the cylinder 55.

Advantageous Effects

The present invention having the configuration described above has the following effects.

Further, it is possible to machine not only a block type, but powder type tooth graft material.

Second, all processes are automatically finished after determining a powder or block type tooth bone graft material, putting it into a receiving container, and then putting the receiving container in a cylinder, the manufacturing time can be reduced to ⅓ to 1/10 of that of the related art by a magnetic vibrator. Accordingly, for a self-tooth bone graft material, a tooth bone graft material can be manufactured within about 25 minutes, thus it is possible to directly operate on a patient after machining a non-treatable tooth extracted from the patient into bone graft material.

Third, the present invention provides automated equipment, so it is possible to machine a tooth bone graft material without the bone graft material being exposed to external contaminants.

Fourth, it is possible to machine a complex block type graft material having not only a simple block bone structure, but a cortical bone structure and a cancellous bone structure.

Fifth, it is possible to selectively adjust the ratio of an inorganic substance and an organic substance of a tooth bone, so it is possible to manufacture a tooth bone graft material suitable for a state to be treated.

BRIEF DESCRIPTION OF THE DRAWINGS

FIG. 5 is a view showing components of the present invention and a control flow.

FIG. 6 is a view showing the flow of a manufacturing process of the present invention.

DETAILED DESCRIPTION OF THE PREFERRED EMBODIMENTS

Figure 1:
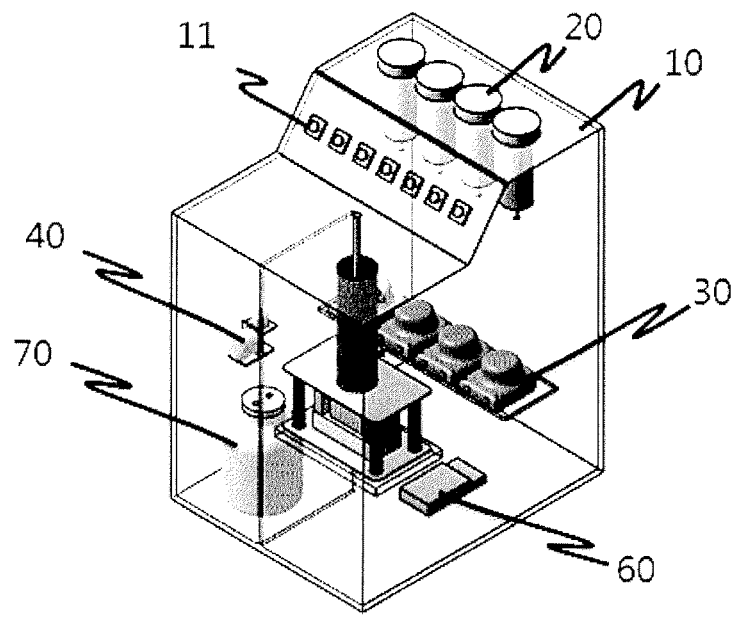
FIG. 1 is a perspective view of an embodiment according to the present invention.

Hereinafter, exemplary embodiments of the present invention will be described in detail with reference to the accompanying drawings for those skilled in the art to be able to easily accomplish the present invention. However, the present invention may be achieved in various different ways and is not limited to the embodiments described herein.

In the accompanying drawings, parts not related to the description (pipes, electronic circuits, and a controller) will be omitted in order to clearly describe the present invention, and like reference numerals will be used to describe like components throughout the specification.

The sizes and thicknesses of the components shown in the drawings were freely selected for convenience of description, so the present invention is not limited thereto. Thicknesses were enlarged in the drawings to clearly show several parts and regions. Further, the thicknesses of some parts and regions were exaggerated for convenience of description.

The present invention relates to an automatic machine for processing a tooth into a bone graft material and, more particularly, an automatic machine for processing a tooth into a graft material that can supply a reagent containing organic substances and inorganic substances of which the contents can be adjusted, in a predetermined amount, with a powder type graft material in a container, and that includes a heat generator and a vibrator for rapidly manufacturing a graft material.

Figure 2:
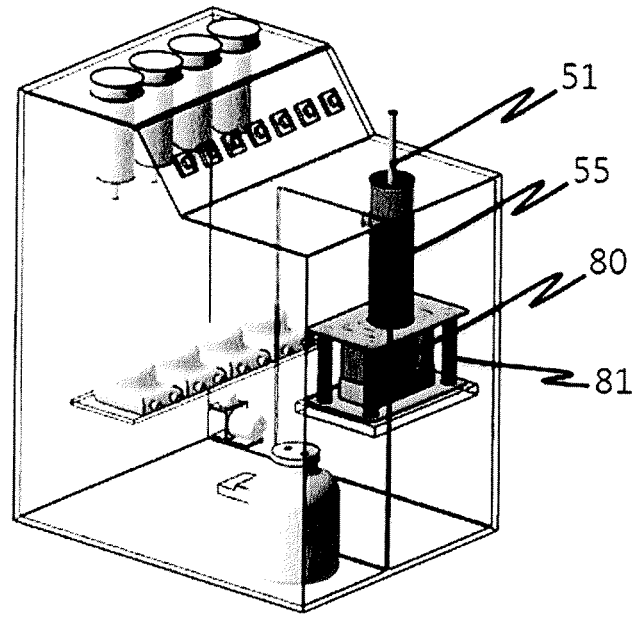
FIG. 2 is another perspective view of an automatic machine for a tooth graft material.
Figure 3:
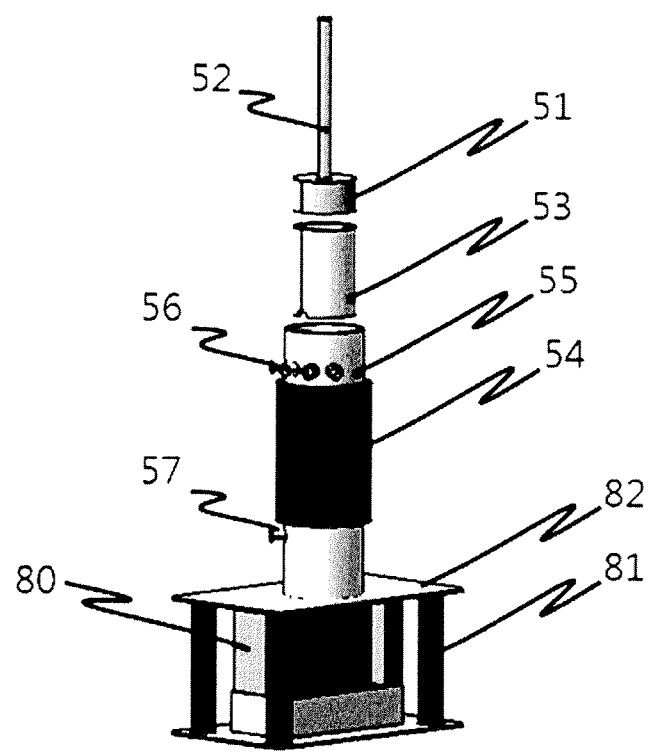
FIG. 3 is a view showing in detail a graft material receiving container 53 and a cylinder 55.

FIG. 1 is a perspective view of an embodiment according to the present invention, FIG. 2 is another perspective view of the automatic machine for processing a tooth into a bone graft material, seen at another angle, FIG. 3 is a view showing in detail a graft material receiving container 53 and a cylinder 55, and FIG. 5 is a view showing components of the present invention and a control flow The present invention includes: a body 10 that includes a power supply 60 supplying power to a controller that controls the amount of supply solution, and a suction pump 40 and a vibrator 80, the body 10 having a receiving space defined by a frame; a receiving container 53 that is disposed in the receiving space, has a space for keeping a tooth bone graft material, and includes a net 59, through which the supply solution can flow inside, and a cover 51 having a handle for convenience work; a cylinder 55 that has a space for keeping the receiving container 53, inlets 56 for supplying the supply solution, and outlets 57 for discharging the supply solution; a vibrator 80 that is fastened to a side of the cylinder 55 and generates vibration of 1 to 100,000 VPM; a supplying container 20 for supplying the supply solution to the cylinder 55; and a suction pump 40 that discharges solution in the cylinder 55 to a discharging container 70.

The present invention further includes a heat generator 54 that covers the cylinder 55 and the supplying container 20 to heat the supply solution therein.

The heat generator 54 heats the solution in the cylinder 55 and the supplying container 20 in the processes of washing, sterilizing, removing inorganic substances, removing fat, and removing protein and keeping the temperature of the solution in the cylinder at 61~120° C. for 10 seconds to 60 minutes.

A solenoid valve that allows for and blocks the supply solution may be disposed in the inlets 56 and the outlets 57 of the cylinder 55. The solenoid valves operate in response to a control signal from the controller.

The supplying container 20 keeps a reagent for the manufacturing process of a graft material, such as sterilized distilled water, trichloromethane, ethyl alcohol, hydrogen peroxide, citric acid, hydrochloric acid (HCl), sulfuric acid, phosphoric acid, malic acid, trichloroacetic acid, sodium hypochlorite (NaClO), sodium hydroxide (NaOH), and glacial acetic acid, and a mixture of the reagent.

Further, the supplying container 20 may be positioned higher than the cylinder 55 to smoothly supply the supply solution.

For a finer supply of a reagent, a fixed-quantity pump 30 that supplies the supply solution in the supplying container 20 in a predetermined amount may be further provided between the supplying container 20 and the cylinder 55.

The fixed-quantity pump 30 supplies a necessary amount of supply solution to the cylinder 55 so that an operator can control the contents of inorganic substances and organic substances in accordance with the purpose of an operation.

The controller may control whether to open/close the solenoid valves, whether to operate the fixed-quantity pump, the control method of the fixed-quantity pump, whether to operate the suction pump 40, and determine control and frequency of vibration of the vibrator 80 in order to control of the supply solution, and may inform a display of the operation states of the components and related information.

In order to accelerate washing and sterilizing, in addition to putting a graft material into a chemical, the vibrator 80 may include a vibrator directly fastened to the cylinder 55 and using an electromagnet, and a spring 81.

The spring 81 can be replaced by damping rubber or an elastic member.

The magnetic vibrator 80 generates vibration of 1 to 100,000 VPM (Vibrations per Minute, the number of vibrations of an electromagnet per minute), is directly connected to the cylinder, and has an oscillating wave higher than ultrasonic waves used in the related art, so the manufacturing time can be reduced.

The cylinder 55 and the receiving container 53 need to be made of a material that suppresses habitation of bacteria, viruses, and molds, has chemical resistance against the supply solution, and a heat resistance against generated heat.

Figure 4:
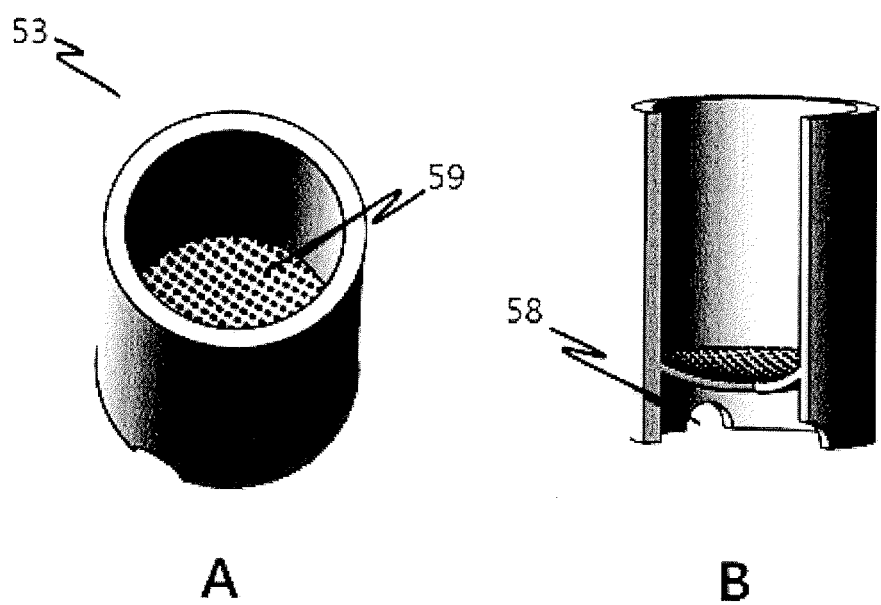
FIG. 4 is a view showing the container 53 in detail.

FIG. 4 is a view showing the receiving container 53 in detail.

In order to process a powder type graft material, the present invention has a space for keeping a tooth graft material to keep a powder type graft material formed by crushing a tooth graft material and includes the net 59 through which a supply solution flows inside and the cover 51 having the handle 52 for convenient work.

The net of the receiving container 53 has fine holes of 1 to 2,000 micron to smoothly receive and discharge the solution in the cylinder 55.

The net 59 may have a shape inclined to a side or a semispherical shape to easily discharge a supply solution.

FIG. 6 shows an automatic manufacturing process of the present invention in a process of manufacturing a tooth bone graft material. As shown in FIG. 6, according to the present invention, all processes of removing a chemical after washing in a process of removing inorganic substances or processes of removing organic substances are automatically performed.

Manufacturing processes of the present invention are described in detail. A method of removing organic substances and inorganic substances from a tooth graft material is described in detail in KR 10-2012-0144121 by the inventor(s).

The steps of primary sterilizing and removing foreign substances are to remove germs on a tooth and to perform primary sterilizing by putting the tooth in hydrogen peroxide (3~35%) for 1 minute to 10 hours in order to remove tartar on the tooth and soft tissue.

A designing step and a boring step are used only for a block type. The designing step involves cutting a graft material in a shape appropriate to a part wherein a tooth has been removed and the boring step is to form fine holes (30~80 holes for one graft material) in a predetermined rectangular pattern of 0.5~0.8 mm using a laser or a drill to process a cancellous bone. The fine holes help the action of a chemical and makes designing easy when the graft material is implanted into the bone inside a gum (alveolus).

A coating step is to prevent a supply solution to be supplied in order to ensure a cortical bone. The coated portion of the cortical bone further suppresses the action of a chemical, as compared with the cancellous bone in the machining process. A coating material in this step is a material having adhesiveness and a stable chemical structure. Further, the material does not influence the machining chemical.

A crushing step, which makes a graft material into a powder type, crushes a tooth in an appropriate graft material size.

A powder type or a block type graft material that has undergone the steps is put into the receiving container 53 and then the receiving container sealed with the cover 51.

The sealed receiving container 53 is put into the cylinder 55 and then the automatic machine is operated.

The controller controls the fixed-quantity pump 30, the vibrator 80, the heat generator 54, the suction pump 40, and the solenoid valves in accordance with a predetermined program and settings of the controller 11.

In a step of removing inorganic substances or removing organic substances, when it is a powder type, citric acid, hydrochloric acid (HCl) of 1~50%, sulfuric acid, citric acid of 1~20%, phosphoric acid, malic acid, and trichloroacetic acid may be independently used of their mixtures may be used to remove inorganic substances, whereas sodium hypochlorite (NaClO) of 1~99%, sodium hydroxide (NaOH) of 1~99%, and glacial acetic acid may be independently used or their mixtures may be used to remove organic substances.

When it is a block type, in the step of removing inorganic substances, the concentration of hydrochloric acid may be in the range of 1~50% to adjust pH of the citric acid (1~20%).

A solution that is supplied to the cylinder 55 is a chemical having a volume of 2~40 times of the volume of a graft material, and inorganic substances or organic substances are removed from the powder by the magnetic vibrator 80 at 100~100,000 VPM (the number of vibrations of an electromagnet per minute) for 1~20 minutes. The process is kept until 1~50% of calcium or collagen remaining in the power is removed. Heat of 61~120° C. is applied to the receiving container 53 for 1 to 20 minutes by the heat generator 54.

In a step of removing a coating, the coating is removed by vibration within 1 to 50 minutes after the step of removing inorganic substances is started. A coating material in this step is a material having adhesiveness and a stable chemical structure. Further, the material does not influence the machining chemical.

In a chemical removing step and a vacuum suction step, the supply solution in the cylinder 55 is discharged to the discharging container 70 by opening the solenoid valves in the outlet 57 and operating the suction pump 40.

In a washing step, sterilized distilled water is supplied by 2~40 times the volume of the graft material and then washing is performed with vibration of 100~100,000 VPM. Further, heat of 61~120° C. is applied to the cylinder for 1 to 20 minutes.

In steps of removing fat and protein, the sterilized distilled water is discharged and then the chemical with fat and protein removed is supplied to the cylinder. A chemical containing trichloromethane and ethyl alcohol that are 2~40 times the volume of the graft material is supplied, and fat and protein are removed by vibration of 100~100,000 VPM. Further, heat of 61~120° C. is applied to the cylinder for 1 to 20 minutes.

In a sterilizing step, hydrogen peroxide of 2~40 times of the volume of the graft material is supplied, and fat and protein are removed by vibration or 100~100,000 VPM. Further, heat of 61~120° C. is applied to the cylinder for 1 to 20 minutes, and then the chemical is discharged.

A graft material is manufactured in the shape that an operator wants through third to tenth washing steps in the step of removing inorganic substances of the present invention.

The manufactured graft material is directly used for a patient, or kept after freezing/drying and sterilizing.

According to the present invention, it is possible to manufacture not only a block type tooth graft material, but a powder type tooth graft material.

Further, all processes are automatically finished after determining the type of a tooth bone graft material, putting it into a receiving container, and then putting the receiving container in a cylinder, the manufacturing time is ⅓ to 1/10 of that of the related art by a magnetic vibrator. Accordingly, a tooth bone graft material can be manufactured within about 25 minutes, so it is possible to directly operate a patient after machining a tooth pulled out from the patient.

Further, the present invention provides automated equipment, so it is possible to machine a tooth bone graft material without being exposed to external contaminants.

INDUSTRIAL APPLICABILITY

The present invention is available for a machine that automatically manufactures a tooth bone graft material that is used for dental implantation and guided bone regeneration (GBR).

What is claimed is:

1. A system for preparing bone graft material, comprising:
    at least one tooth;
    an automatic machine for processing the at least one tooth into bone graft material, comprising:
    a body including a power supply supplying power to a controller and the controller, which controls the amount of a supply solution for removing organic and inorganic substances from the at least one tooth, and operation of a suction pump and a vibrator, and having a receiving space defined by a frame; a receiving container made of a material which has bacteria resistance, chemical resistance and heat resistance disposed in the receiving space, having a space for keeping a bone graft material made from the at least one tooth, and including a net having fine holes of 1 to 2000 micron, through which the supply solution can flow inside, and a solid sealing member accommodated inside a cylinder for sealing the receiving container and a handle disposed on a top surface of the solid sealing member opposite to the net for convenience work;
    the cylinder having a space for keeping the receiving container, inlets for supplying the supply solution, and outlets for discharging the supply solution;
    the vibrator for removing fat and protein in the at least one tooth by vibration fastened to a side of the cylinder and generating vibration of 1 to 100,000 VPM;
    a supplying container for supplying the supply solution to the cylinder; and
    the suction pump discharging a solution in the cylinder to a discharging container,
    wherein the vibrator accelerates washing and sterilizing and is directly fastened to the cylinder, and a plurality of springs surround the vibrator.

2. The system for preparing bone graft material of claim 1, wherein the automatic machine further comprises: a heat generator covering the cylinder and the supplying container to heat the supply solution therein.

3. The system for preparing bone graft material of claim 1, wherein the automatic machine further comprises: a fixed-quantity pump supplying the supply solution in the supplying container in a predetermined amount, between the supplying container and the cylinder.

4. The system for preparing bone graft material of claim 1, wherein the at least one tooth is one of a human tooth or an animal tooth.

* * * * *